United States Patent [19]

Källenius et al.

[11] Patent Number: 4,762,824
[45] Date of Patent: Aug. 9, 1988

[54] COMPOSITIONS AND METHODS USEFUL FOR UROPATHOGENIC BACTERIAL IDENTIFICATION OR DIAGNOSIS AND INHIBITION OF ADHERENCE OF UROPATHOGENIC BACTERIA TO CELLS HAVING A STRUCTURAL ELEMENT SIMILAR TO THAT OF THE ACTIVE PRINCIPLE OF THE INVENTION

[75] Inventors: Gunilla P. Källenius, Enskede; Karl A. Lundblad, Uppsala; Nils R. Möllby, Gustavsberg; Stefan B. Svensson, Stockholm; Jan Winberg, Stockholm, all of Sweden

[73] Assignee: Svenska Sockerfabriks AB, Malmö, Sweden

[21] Appl. No.: 892,807

[22] Filed: Aug. 1, 1986

Related U.S. Application Data

[62] Division of Ser. No. 317,894, filed as PCT SE81/00065 on Mar. 5, 1981, publish as WO81/02520 on Sep. 17, 1981, Pat. No. 4,657,849.

[30] Foreign Application Priority Data

Mar. 5, 1980 [SE] Sweden .............................. 8001748

[51] Int. Cl.$^4$ ................... A61K 31/700; A61K 35/18; A61K 39/00; C07G 3/00
[52] U.S. Cl. ........................................ 514/54; 514/12; 514/2; 536/1.1; 536/4; 536/123; 536/18.7; 536/54
[58] Field of Search .................. 514/54, 12, 2; 536/1, 536/4, 1.1, 123

[56] References Cited

U.S. PATENT DOCUMENTS 4,137,401  1/1979  Lemieux et al. .................. 536/116
4,238,473  12/1980  Lemieux et al. .................. 424/11

OTHER PUBLICATIONS

J. Urol. 1, 472–476 (1977).
Lancet. ii, 540–543 (1978).
FEMS Microbiol. Lett. 5, 295–299 (1979).
J. Immunol. Meth. 25, 323 (1979).
Immunol. Meth. enzymol. L, part C, 163–171 (1978) (Two papers).
JACS 97:14, 4076 (1975).
Arch. Biochem. Biophys. 175, 661 (1976).
J. Immunol., 120, 1750 (1978).
In Meth. enzymol., L, part C, 155 (1978).
J. Immunol. Meth. 17, 249 (1977).
Proc. Nat. Acad. Sci., USA 73 (1976), 3263–3267.
Carbohydrate Research 62, 245–252 (1978).
Carbohydrate Research 74, 105–116 (1979).
Carbohydrate Research 63, 139–147 (1978).
Berichte 34, 945–(1901).
In: Methods in Enzymology, vol. 28B, ed. V. Ginsburg, p. 212, Academic Press, New York, (1972).
Journal of Urology, vol. 131, pp. 163–167 (Jan. 1984).
Journal of Urology, vol. 133, pp. 1068–1075 (Jun. 1985).
Källenius, *Infection,* (Munich) 1980, 8 (Supl 3) 288 in Chem Abs., vol. 93, 1980, 183837r.

*Primary Examiner*—Ronald W. Griffin
*Attorney, Agent, or Firm*—Gordon W. Hueschen

[57] ABSTRACT

Compositions and methods useful for identification or diagnostic use, or inhibition of adherence of uropathogenic bacteria to cells, all in connection with uropathogenic bacterial infections, containing as an active constituent the structural element, preferably in terminal position:

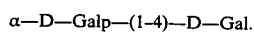

α—D—Galp—(1-4)—D—Gal.

Process for identification or quantification of such structural element in native biological material from mammals including man, comprising using antibodies, the generation of which has been initiated by such composition. A process for the identification of bacterial acceptor structures (pili, syn. fimbriae) recognizing the described structural element, comprising using this recognition. A process for purifying acceptor structures of bacteria, comprising using for the purification the affinity between such structural element and the corresponding acceptor structures on the bacteria. A method of diagnosing mammals including man in regard to a tendency toward bacterial infection involving such receptor structure, comprising generating antibodies against said receptor structure and recording the reaction of said antibodies and cells from the mammal.

19 Claims, No Drawings

COMPOSITIONS AND METHODS USEFUL FOR UROPATHOGENIC BACTERIAL IDENTIFICATION OR DIAGNOSIS AND INHIBITION OF ADHERENCE OF UROPATHOGENIC BACTERIA TO CELLS HAVING A STRUCTURAL ELEMENT SIMILAR TO THAT OF THE ACTIVE PRINCIPLE OF THE INVENTION

This is a division of application Ser. No. 317,894, filed as PCT SE81/00065 on Mar. 5, 1981, published as WO81/02520 on Sept. 17, 1981, now U.S. Pat. No. 4,657,849, issued Apr. 14, 1987.

TECHNICAL FIELD

The present invention relates to compositions and methods which are useful for the identification and/or diagnosis of uropathogenic bacteria, and the inhibition of adherence of urophathogenic bacteria (the type of bacteria responsible for urinary tract infection) to cells having a structural element which is similar to that present in the active principles of the present invention, so that the bacteria recognizes the structural element of the active principle rather than that of the cell.

BACKGROUND ART

Most bacterial infections arise from attack of bacteria on mucous membranes. For establishment of such infections, the initial ability of the bacteria to adhere to epithelium surfaces is of the greatest importance. The infectious capacity of gram-negative bacteria (for example *Escherichia coli*) is thus directly related to the ability of the bacterium to adhere to epithelium cells (Jones, J. G., Ref. 1). *E. coli* bacteria adhere more readily to epithelic vaginal cells from women showing a tendency for urinary tract infections as compared to epithelial vaginal cells from healthy controls (Fowler et al., Ref. 2). Correspondingly, investigations both in vivo and in vitro have shown that a larger number of bacteria adhere to periurethral epithelium cells from urinary tract infection-prone girls as compared to the corresponding cells from healthy controls (Kallenius et al., Ref. 3).

The importance of carbohydrate structures on cell surfaces for biological recognition (i.e., receptors) has been recognized including the recognition of the bacterium by mammalian cells (Ref. 1) necessary for adherence thereto. Studies have shown that the adhesion of several uropathogenic *E. coli* strains to periurethral cells is correlated to the ability of specifically agglutinating human erythrocytes (Kallenius et al., Ref. 4). From this the conclusion can be drawn that which is some substance, possibly of a carbohydrate character, present on the surface of human erythrocytes, is the receptor which is recognized by such urinary tract pathogenic bacteria and necessary for adherence of the bacteria to the surface thereof.

SUMMARY OF THE INVENTION

The present invention has for its purpose to provide a composition or a substance having the ability to replacing the normal in vivo receptor function in of cells relation to pathogenic bacteria infections in man and animals.

Another object of the invention is to provide such composition or substance which in addition to bacterial identification use also can be used diagnostically.

Yet another object of the invention is to provide a process for identification or quantification of receptor structures in native biologic material from mammals including man. The invention also relates to a process for purification of acceptor structures of bacteria and their recognition of the structural element of the present invention in preference to their recognition of cells to which said bacteria might otherwise adhere.

The invention is particularly related to receptor structures for uropathogenic *E. coli* strains.

In connection with studies and experiments leading to the present invention it has been found that the receptor for uropathogenic bacteria exposed on the surface of human erythrocytes contains a structural element of the minimum formula:

α—D—Galp—(1-4)—D—Gal  (Jones et al., Ref. 12)

A particularly preferred structural element has the formula:

α—D—Galp—(1-4)—β—D—Galp

The active constituent in the composition according to the invention thus contains as an active constituent a structural element suitably having the formula:

α—D—Galp—(1-4)—α[or β]—D—Galp—1—O—R

In this formula the symbol R signifies a nontoxic and noninterfering organic residue which is bound in either α or β-configuration and which is of an arbitrary type as long as it does not adversely effect the circumstances in connection with the use of the composition i.e., as long as it is nontoxic and noninterfering.

Within this definition the following compounds are of particular interest:

α—D—Galp—(1-4)—β—D—Galp—1—O—φ—NO₂ (p-Nitrophenyl 4—O—α—D— galactopyranosyl — β — D— galactopyranoside);

α—D—Galp—(1-4)—β—D—Galp—(1-4-)—β—D—Glcp—1—O—φ—NO₂ (p—Nitrophenyl 4—O—(4—O—α—D—galactopyranosyl-)—β—D—galactopyranosyl—β—D—glucopyranoside);

α—D—Galp—(1-4)—β—D—Galp—1—O—Me (Methyl 4—O—α—D—galactopyranosyl—β—D—galactopyranoside);

α—D—Galp—(1-4)—β—D—Galp—(1-4-)—β—D—Glcp—1—O—Me (Methyl 4—O—(-4—O—α—D—galactopyranosyl)—β—D—galactopyranosyl—β—D—glucopyranoside); and α—D—Galp—(1-4)—β—D—Galp—1—O—φ—NHCSNH—(CH₂)₁₁—CH₃ (4—(N-'—dodecylthioureido)—phenyl 4—O—α—D—galactopyranosyl—β—D—galactopyranoside).

The structural element in question with the above given minimum formula is preferably positioned in omega or terminal position, i.e., with the left end according to the formula in a freely exposed state.

Additional preferred structural elements comprise the following:

a—D—Galp—(1-4)—α—D—Galp,
a—D—Galp—(1-4)—βD—Galp—(1-4-)—β—D—Glc,
a—D—Galp—(1-4)—β—D—Galp—(1-4-)—α—D—Glc,
a—D—Galp—(1-4)—β—D—Galp—(1-4-)—α—D—Glcp—1—O—R, a—D—Galp—(1-4)—B—D—Galp—(1-4-)—β—D—Glcp—1—O—R, a—D—Galp—(1-4)—β—D—Galp—(1-4)—D—Glucitol, a—D—Galp—(1-4)—β—D—Galp—(1-4-)—α—D—Glcp—1—O—Me, and a—D—Galp—(1-4)—β—D—Galp—β—D—GlcNAcp—(-1-3)—β—D—Galp—(1-4)—D—Glc.

According to another aspect of the invention there is provided a compound comprising the above structural element together with a pharmaceutically acceptable carrier or diluent.

According to yet another aspect of the invention there is provided compositions which can be used for example for identification or quantification of the receptor structures in question in native biological material or for identification and purification of acceptor structures of bacteria. The compositions according to the use of the invention in this context contain one or several structural elements according to the above in at least bivalent state, and in covalent association. According to a suitable embodiment of the composition of the invention said structural element is covalently coupled to a macromolecular carrier, possibly via a coupling arm. As such macromolecular carriers there may be used synthetic or naturally occurring polypeptides, polysaccharides or other polymers.

Representative coupling arms between the structural element and the macromolecular carrier can be any of the following:

Preferred structural elements in said type of composition according to the invention are as given above and as given below.

The haemagglutination reaction of human erythrocytes caused by uropathogenic bacteria is due to interaction of acceptor structures (i.e., pili, syn. fimbriae, which are filamentary rigid protrusions of protein nature) on the surface of the bacterium and receptors on the surface of the erythrocytes or other cells containing the above-mentioned structural element. This structural element is considered to be present on the surface of human erythrocytes as a part of the glycosphingolipid trihexosyl ceramide having the formula:

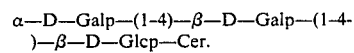

corresponding to the blood group antigen $p^k$. A similar structural element is present on human erythrocytes also as a part of the glycosphingolipid corresponding to blood group antigen $P_1$:

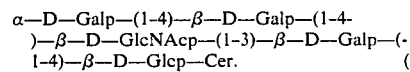

(Marcus et al., Ref. 13)

The above-mentioned glycosphingolipids present on human erythrocytes are found also on the surface of many other cells including epithelium cells. Of particular interest in this connection is the fact that the glycos-

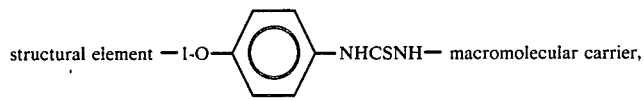

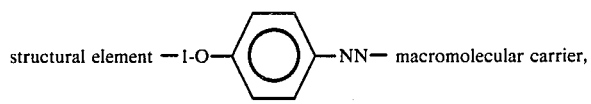

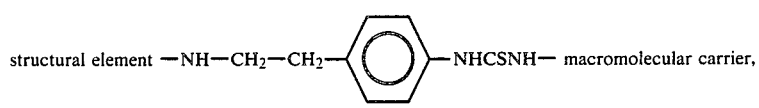

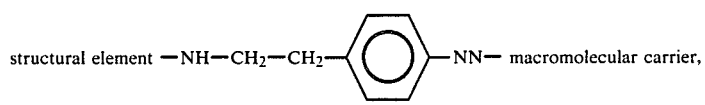

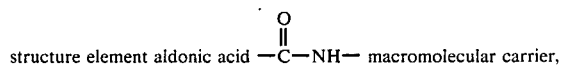

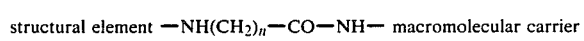

wherein n can vary between 1 and 20.

Where the structural element is linked to an NH group, the linkage is by way of a terminal reducing sugar residue. In the case of the aldonic acid

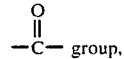 group, the residue is in the form of its aldonic acid.

phingolipid biosyl ceramide of the formula:

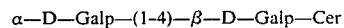

containing the above-identified structural element is richly present in normal human renal tissue.

The fact that human urinary tract epithelium cells from, individuals of $\bar{p}$ phenotype (i.e. individuals lacking the glycosphingolipids P, $P_1$ and $P^k$) show significantly lower binding of urinary tract pathogenic E. coli bacteria strongly suggests that the above mentioned structural elements contained in the compositions according to this invention have influence on the adhering capacity of said bacteria in the urinary tract.

Further evidence that the structural element

α—D—Galp—(1-4)—β—D—Galp constitutes a significant part of the receptor of human cell surfaces is the ability of the substance:

α—D—Galp—(1-4)—β—D—Galp—(1-4)—D—Glucitol to inhibit the agglutination of human erythrocytes of P phenotype, i.e., of $P_1$, $P_2$, $P_1^k$ or $P_2^k$ phenotypes.

EXAMPLES

The invention will in the following be further described by non-limiting examples.

Haemagglutination Test

The strains of bacteria used in the experiments are given in the appended Table 1, and out of the strains shown therein all except strain T1 have been isolated from children having acute pyelonephritis. The twenty faecal strains of E.coli were obtained from 20 healthy individuals, and one strain, H10407, was obtained from D. J. Evans (Evans, D. G., Evans, J. D. J. and Tjoa, W. (1977). Infect Immun. 18, 330–337) was also studied.

Erythrocytes were obtained from bovines, guineapigs, adults and umbilical cord blood. Erythrocytes from individuals of the p̄, Vel(—) and Kp(b—)-phenotypes were obtained from the blood bank at the University Hospital in Umea, and erythrocytes from a $P_1^k$-donor were obtained from Dr. H. Nevanlinna (Helsinki Red Cross Blood Central).

Blood samples were collected in 1% (weight-volume) sodium citrate or in acid citrate dextrose (ACD) and, after washing four times in phosphate buffer saline solution (PBS), pH 7.2, the erythrocytes were suspended in PBS to 3% and used the same day. Haemagglutination tests were performed in a conventional manner (Källenius, G. and Möllby, R. (1979). FEMS Microbiol. Lett. 5, 295–299). (Ref. 4)

In brief it can be said that the bacteria were grown overnight on CFA-agar (Evans, D. G., Evans, J. D. J. and Tjoa, W. (1977). Infect. Immun. 18, 330–337), and suspended in PBS to $5 \times 10^9$ bacteria per ml. Serial dilutions were carried out in PBS while using 50 μl diluent in microtiter plates (Linbro Sc. Comp. Inc., Hamden, Conn.). To each well there were then added 50 μl PBS and 50 μl of the erythrocyte suspension for ivestigation. The haemagglutination titer was then determined after incubation at 4° C. for one hour as the reciprocal of the highest dilution giving visible agglutination of the erythrocytes. In all cases parallel experiments were carried out with 40 mM D-mannose.

The results of these haemagglutination experiments are shown in appended Table 1, from which it is clear that the pyelonephritic E.coli strains all gave haemagglutination with human erythrocytes. Contrary to this little or no agglutination was obtained when using the faecal strains (Table 1).

For haemagglutination-inhibition tests there were used serial dilutions of the relevant inhibitor (active constituent) (50 μl/well) and an equal volume of the bacterial suspension diluted to obtain twice the lowest haemagglutinating concentration. After 30 seconds of mixing there were added to each well aliquot quantities (50 μl) of the test erythrocytes, and the inhibitory effect was then recorded.

EXAMPLE 1

Preparation of Oligosaccharides Containing the Structural Element α—D—Galp—(1-4)—D—Gal

A.

α—D—Galp—(1-4)—β—D—Galp—(1-4)—D—Glucitol

Erythrocytes from discarded blood of blood groups A, B, AB and O were lysed and the membranes were isolated by means of centrifugation. In this manner about 10 g of membranes from one liter of blood were obtained. The membranes were pretreated by the process according to Dodge, J. T., Mitchell, C., and Hanahan, D. J. (1963), Arch. Biochem. Biophys. 100, 119–130, i.e., homogenized, suspended in water and lyophilized.

To 50 g of the lyophilized material there is added trifluoroacetic acid anhydride (1.25 l) and trifluoroacetic acid (1.25 l), and the reaction mixture is heated at about 100° C. in a tube of acid-resistant stainless steel at about 4 atms. overpressure for a period of time of about 48 hours.

After this treatment the reaction mixture is cooled and evaporated to dryness, there being obtained a dark to black-coloured residue. To this residue there is added methanol (700 ml), and the mixture is evaporated to dryness. The residue is then diluted with 50% aqueous solution of acetic acid (1000 ml) and is allowed to stand at room temperature for about 18 hours. The reaction mixture is filtered with a glass filter and evaporated to dryness.

The obtained residue is distributed between water and diethyl ether. The ether phase is washed 4 times with water and the combined aqueous washings are washed 4 times with diethyl ether. The aqueous solution obtained is yellow and contains the released oligosaccharides.

The oligosaccharides are purified by gel chromatography followed by preparative paper chromatography, and the purification procedure is followed by gas chromatography-direct mass spectrometry.

In haemagglutination inhibition tests, the above-described oligosaccharide is found effectively to inhibit the haemagglutination caused by pyelonephritogenic E. coli strains. This fact shows that the oligosaccharide prevents interaction between the bacteria and the receptors of the human erythrocytes.

B.

The inhibition test according to A was repeated but using a disaccharide derivative of the formula:

α—D—Galp—(1-4)—β—D—Galp—1—O—φ—NO₂

The compound was synthesized in the following manner:

The octaacetate of 4—O—α—D—Galp—α,-β—D—Galp (Cox et al., Ref. 14) was treated with hydrogen bromide in glacial acetic acid. The formed acetobromo disaccharide derivative was treated with sodium p-nitrophenoxide according to the well-known procedure of Shah et al. (Ref. 15). After purification on silica gel the product was de—O—acetylated with sodium methoxide in methanol to yield the compound.

This disaccharide derivative is found to inhibit the haemagglutination reaction in the same manner as shown above under A.

C.

The inhibition test according to A above is repeated, there being used as an inhibitor the saccharide derivative having the formula:

α—D—Galp—(1-4)—β—D—Galp—(1-4-)—β—D—Glcp—1—O—φ—NO₂

This compound was synthesized in the following manner:

The undecaacetate of 4—O—α—D—Galp—β—D—Galp—α,β—D—Glcp (Cox et al., Ref. 16) was treated with hydrogen bromide in glacial acetic acid. The formed acetobromo trisaccharide derivative was treated with sodium p-nitrophenoxide according to Shah et al. (Ref. 15). After purification on silica gel, the product was de—O—acetylated with sodium methoxide in methanol to yield the compound.

This saccharide derivative is also found to inhibit the haemagglutination reaction.

D.

The above inhibition test is repeated but using a disaccharide derivative of the formula:

α—D—Galp—(1-4)—β—D—Galp—1—O—Me

This compound was synthesized in the following manner:

The acetobromo disaccharide derivative (described above under B) was treated with silver oxide in methanol to yield the β-methyl glycoside according to the standard procedure of Koenigs et al. (Ref. 17). After purification on silica gel the product was de—O—acetylated with sodium methoxide in methanol to yield the compound.

The saccharide derivative was found to inhibit the haemagglutination reaction as described above.

E.

The above inhibition test is repeated but using a saccharide derivative of the formula:

α—D—Galp—(1-4)—β—D—Galp—(1-4-)—β—D—Glcp—1—O—Me

This compound was synthesized according to the procedure of Cox et al., Ref. 16, and it was found to inhibit the haemagglutination reaction.

EXAMPLE 2

Preparation of Compositions Containing the Structural Element in at Least Bivalent State Linked to a Macromolecular Carrier I. The composition is prepared starting from native oligosaccharides containing a free reducing terminal sugar residue. In the preparation sequences diagrammatically shown below, X symbolises the structural element according to the invention, whereas the abbreviation MMB relates to the macromolecular carrier.

a. Following reaction sequences illustrate the preparation of a composition according to the invention containing the active structural element covalently bonded to a macromolecular carrier via a coupling arm.

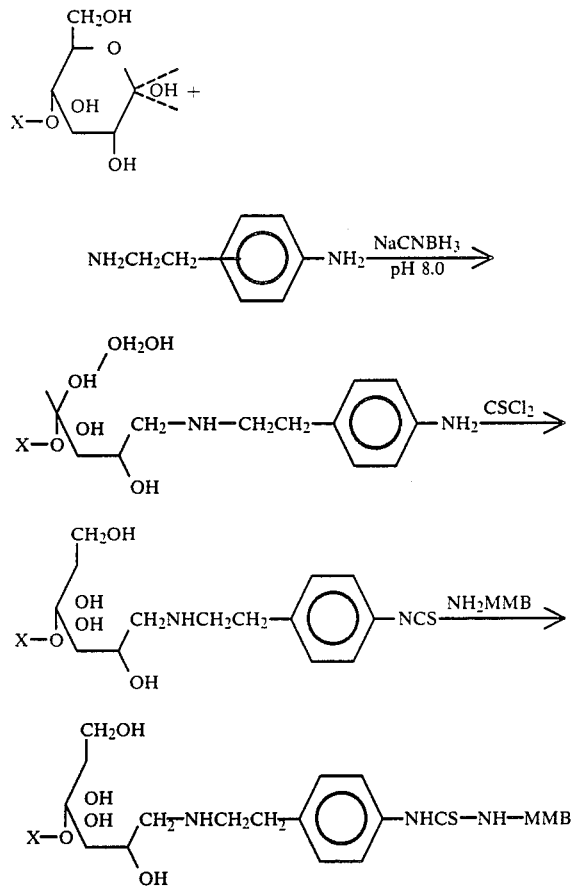

This is the procedure of Svenson et al. (Ref. 5), who employed the same to link an oligosaccharide to proteins such as bovine serum albumin and a polyacrylamide matrix (aminoethylated Bio-Gel P200). The versatility of their method was established by conjugating tetra, octa, and dodecasaccharides to various proteins in high yields, not only to BSA and aminoethylated polyacrylamide gels, but in their own words "also to human serum albumin (HSA) diphtheria toxin, Limulus polyphemues hemocyanine, edestine and outer membrane proteins (porins) from Salmonella typhimurium.

b. The reactions were performed in accordance with Ia above but the p-aminophenethylamine compound was not converted to the corresponding phenyl isothiocyanate compound but was instead diazotized, the diazonium derivative being then reacted with free primary aliphatic amines on the macromolecular carrier.

This was according to the procedure of Svenson et al., (Ref. 5), discussed in the foregoing, as well as the procedure of Zopf et al. (Ref. 6), actually two papers extending from pages 165 through 171 of the reference, who coupled oligosaccharides to edestin and bovine serum albumin employing the stated procedure more fully detailed in the reference.

Svenson et al. also acknowledge, on page 326, their earlier conjunction of oligosaccharides with BSA using the Aldonate method, as well as the work of additional researchers in coupling oligosaccharides to BSA by the Aldonate method as well as by the prior-art recognized Aza coupling method.

c.
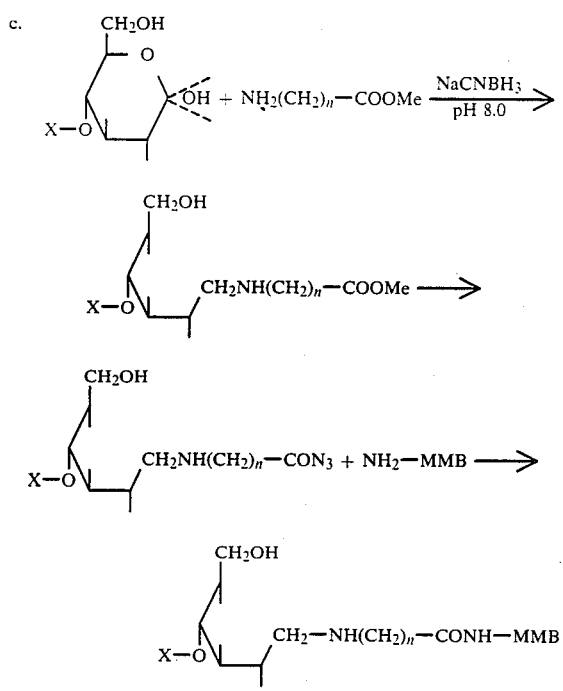

This is the procedure of Lemieux et al. (Ref. 7), who employed the same to conjugate, attach, or covalently bind oligosaccharides to the free amino groups of bovine serum albumin. Attention is also called to Lemieux et al. U.S. Pat. Nos. 4,137,401 and 4,238,473, in which are disclosed the coupling of oligosaccharides to carrier molecules by means of glycosidically-linked bridging arms, as in Ref. 7, the macromolecular molecules disclosed in these patents being aminated glass beads, an agarose matrix, a polyacrylic support, and silylaminated calcined diatomaceous earth, as well as other carriers or supports selected from "the group consisting of antigen-forming proteins, red blood cells, aminated polysaccharides of the type dextran, sepharose, and agarose, aminated glass, aminated polystyrene, polyvinylamine, aminated polyacrylamide, or aminated polyvinyl alcohol, aminated calcined diatomaceous earth, or aminated diatomaceous earth", to quote the patentees, particularly preferred proteins being bovine serum albumin (BSA), human serum albumin (HSA) and polylysine, red blood cells, or polysaccharides such as aminated dextran. As usual, as disclosed, the selected macromolecular carriers "normally are employed as beads as latex particles but may be used on surfaces of tubes and plates depending on the use for the antigenic surface; that is, as an insoluble absorbant for the extraction of antibodies, for the preparation of an affinity chromatographic column, for the detection of agglutination-type phenomena as for spot tests on surfaces", again to quote the patentees.

d.
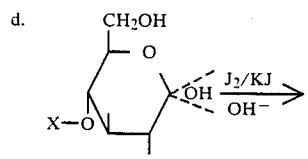

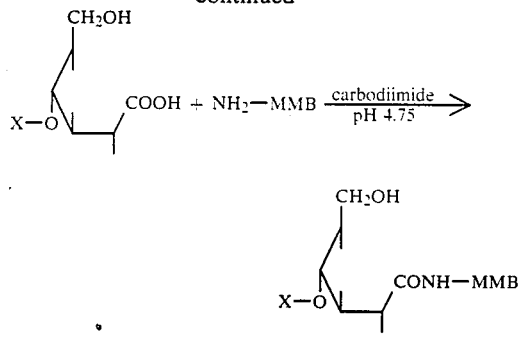

This is the known procedure of Lonngren et al. and Svenson et al., respectively References 8 and 9, for the conjugation of oligosaccharides to proteins by activation of carboxyl groups with water-soluble carbodiimide derivatives after oxidation of the oligosaccharide to its corresponding aldonic acid in line with the foregoing sequence, the macromolecular molecule to which the oligosaccharides were linked including BSA, ovalbumin, and Concanavalin A. The author in Reference 8 also discusses the existing state of the art for such coupling reactions employing reduction by borohydride of a Schiff base formed between a reducing sugar and a protein, the aldonic acid coupling method using a mixed anhydride approach for coupling to BSA or polylysine, and the Lemieux coupling of oligosaccharides to proteins by conversion of the corresponding hydrazides to acylazides via diazotization and recommends the Aldonate coupling procedure as a relatively simple method. The carbodiimide procedure is also disclosed by Lonngren et al. in Meth. Enzymol. L, part C, at pages 160–162.

e.
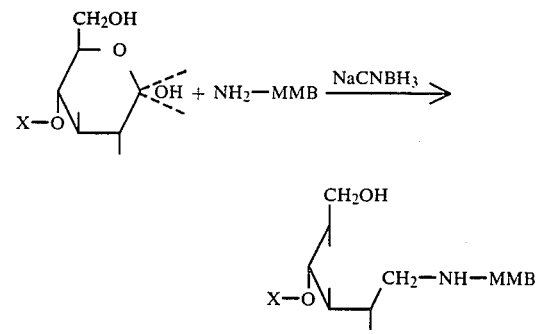

This procedure for the coupling of carbohydrates to proteins by reductive amination with cyanoborohydride is disclosed by Gray (Ref. 10) who coupled oligosaccharides to BSA according to this procedure and also reviewed the state of the art regarding coupling procedures in general.

f. The preparation of compositions that contain the active element as defined could also be performed by incorporation of synthetic glycolipids, as further discussed in the following text, into liposomes or erythrocytes or other lipophilic carriers.

EXAMPLE 3

Characterization of the Receptor of MRHA$_{hum}$

In this context MRHA$_{hum}$ means "mannose resistant haemagglutination of human erythrocytes".

Treatment of human erythrocytes with α-galactosidase reduces their haemagglutination. This is an indication that α-D-galactopyranoside groups in a terminal position is of particular importance in the receptor structure.

The para-nitroderivatives and the methyl derivatives of the di- and trisaccharides, i.e. compounds of Examples 1B, 1C, 1D and 1E, were found effectively to inhibit MRHA$_{hum}$ with different pyelonephritogenic strains of E. coli and with blood from different donors. This indicates the fact that the glucose molecule is of less significance, since no difference between the di- and the trisaccharides regarding inhibitory capacity was noted.

Erythrocytes from guinea-pigs and from p̄-individuals, normally not reacting with P-fimbriae, were coated with purified trihexosyl ceramide (THC). These erythrocytes then reacted with MRHA$_{hum}$ with P-fimbriae-containing E.coli. Thus, THC acts as a receptor for haemagglutination. The test was performed both with commercial THC (Supelco, USA) and with THC prepared from hog intestinals by A. Lundblad and S. Svensson, Lund, Sweden.

This synthetic disaccharide was converted to the corresponding p-isothiocyanotophenyl derivative and was reacted with dodecyl amine in order to yield the synthetic glycolipid according to the formula:

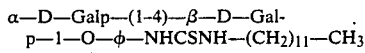

α—D—Galp—(1-4)—β—D—Gal-
p—1—O—φ—NHCSNH—(CH$_2$)$_{11}$—CH$_3$

This compound was synthesized in the following manner: The compound under Example 1B above was hydrogenated using Adam's catalyst (PtO$_2$). The formed p-aminophenyl glycoside was converted to the corresponding p-isothiocyanatophenyl glycoside by treatment with thiophosgene, essentially as described in McBroom et al., Ref. 18, which is essentially the reaction of Example 2, Ia as set forth in the foregoing and in Reference 5, further discussed at that point. McBroom et al. coupled carbohydrates to proteins by both diazonium and phenylisothiocyanate reactions, the diazonium approach being further discussed under Example 2 Ib in the foregoing, and showed employment as the protein for conjugation not only BSA, but also human gamma globulin, horse serum globulin, ovalbumin, horse serum albumin, porcine and bovine gamma gobulin, various albumins, and hemocyanine in their review of the art, and in their conjugation using phenylisothiocyanato glycoside derivatives employed bovine serum albumin as the macromolecular carrier. They disclose that this procedure can be extended to other natural or synthetic macromolecules, specifically mentioning solid matrices such as aminoethylcellulose and p-aminobenzylcellulose as solid macromolecular carriers for combination with oligosaccharides in the process. This glycoside was then reacted with dodecyl-1-amine and the formed compound was purified on silica gel. This synthetic glycolipid was used in a corresponding coating test, a positive result being obtained. This test indicates that the results obtained above with preparations made from biological material were not effected by contaminants present in said preparations.

Adhesion tests with uroepithelial cells

Uroepithelial cells in morning urine from individuals of p̄-phenotype were compared in parallel tests with cells from P-individuals with regard to their ability to adhere three strains of pyelonephritogenic E.coli with P-fimbriae. In the same way as the erythrocytes p̄-cells bound significantly lower quantities of bacteria (p<0.02). Since these individuals lack the receptor structure on their epithelial cells, this also confirms the fact that the structure in question acts as a receptor also for adhesion to urinary epithelium.

The adhesion to uroepithelial cells (of P-type) of pyelonephritogenic E.coli was effectively inhibited by the synthetic disaccharide derivative (the compound of Example 1D above). This proves that the disaccharide structure is a receptor structure involved in adhesion to epithelial cells.

The adhesion to the same cells was increased about threefold by adding the para-nitrophenyl derivative of the trisaccharide (the compound of Example 1C above), since the lipophilic para-nitrophenyl group was associated with the lipophilic membrane of the cell to result in coating. This shows that also adhesion to epithelial cells is obtained by coating the cells with a synthetic receptor substance.

EXAMPLE 4

Preparation of Antibodies Having Specificity Towards the Structural Element in Question a. Preparation of monoclonal antibodies by hydridoma technique.

I. Balb/c-mice are immunized with a composition according to Example 2 or 3. The spleen from hyperimmunized animal is harvested and a cell suspension is prepared by mechanical comminution of the tissue. After gradient centrifugation to obtain a pure cell preparation, the cells are fused by means of polyethylene glycol (PEG average molecular weight 1500) with established B-myeloma cell lines from Balb/c-mice according to known technique. After cloning of the hybridoma cells generating the antibody desired, the cells are propagated on a large scale, the culture medium supernatants being harvested and the antibodies being purified in a conventional manner. For identifying antibody generating clones there is used so-called enzyme-linked immunosorbent assay (ELISA).

This is the method of Svenson et al. (Ref. 11) and Svenson et al. (Ref. 9) for the quantitation of antibody titers in a rabbit immunized with an oligosaccharide-protein conjugate (or other immunizing agent) which is many times more sensitive than a single radial immunodiffusion assay, as set forth in the cited references. The test is employed to confirm both oligosaccharide and carrier protein specificity.

II. Mammals are immunized with an oligosaccharide protein or polymer composition according to Example 2 or 3. Antibodies are isolated from the hyperimmune serum of the mammal and purified in accordance with conventional techniques.

EXAMPLE 5

Test for Identification of Bacteria Having Acceptor Structure Showing Specificity Towards the Structural Element in Question a. Bacteria are incubated with human erythrocytes of P phenotype. As negative control cells there are used human erythrocytes of p̄ phenotype. Positive haemagglutination of P but not of p̄ erythrocytes verifies the fact that the bacterium in question possesses acceptor structures. The test is performed in accordance with haemagglutination technique previously described.

b. *E.coli* bacteria are incubated with a composition wherein the structural element in question is covalently or by other association in multivalent form bonded to a particular matrix according to Example 2 or 3. Incubation is performed on slides for about 15 minutes, the preparation being then studied in light microscope. By positive reaction the particles are found to be totally covered by bacteria adhering to the receptor structures of the particles. With negative reaction the particles are wholly free from bonded bacteria.

c. *E.coli* bacteria are mixed with a composition according to Example 2 or 3 direct on slides, positive reaction resulting in an agglutination reaction visible to the naked eye. The receptor structures described in this disclosure result in positive reaction.

EXAMPLE 6

Purification of Acceptor Structures of Bacteria (pili, syn. fimbriae)

A composition according to Example 2 or 3 above is arranged in the form of a column. *E.coli* bacteria are treated mechanically giving release of the filamentous protrusions (pili). A slurry of the released pili is then passed through the column, the acceptor structures being held in the column by interaction with the receptor structures of the column. After rinsing the column, the acceptor structures maintained therein can be eluted by addition of the disaccharide derivative (described under 1D) and obtained in a purified form. Purified pili can be used in vaccines or for antibody analyses in for example body fluids, such as urine or mother's milk.

In this disclosure the abbreviations used in the structural formulae have the following meaning:

Galp = galactopyranosyl

Glcp = glucopyranosyl
GlcNAcp = 2-acetamido-2-deoxy-glucopyranosyl
Glc = glucose
Cer. = ceramide It should be observed that the invention is not delimited to the embodiments presented in the above examples but that many modifications are possible within the scope of the appended patent claims.

TABLE 1

| Haemagglutination by pyelonephritic and faecal strains of *E. coli*[a] | | | | | | | |
|---|---|---|---|---|---|---|---|
| Pyelone- | Species of erythrocytes | | | | Species of erythrocytes | | |
| phritic strain | hu-man[b] | guinea pig | bo-vine | Faecal strain | hu-man | guinea pig | bo-vine |
| T1 | 16[c] | — | — | SBL393 | — | — | — |
| NK1 | 32 | — | — | SBL405 | — | — | — |
| ER2 | 16 | — | — | SBL410 | 16 | — | — |
| KS14 | 8 | 1 | — | SBL418 | — | — | — |
| KS52 | 256 | — | — | SBL419 | 4 | 4 | 4 |
| KS65 | 8 | 2 | — | SBL423 | — | — | — |
| KS69 | 64 | — | — | SBL489 | — | — | — |
| KS70 | 8 | — | — | SBL490 | — | — | — |
| KS71 | 64 | — | — | SBL493 | 2 | 2 | 2 |
| KS73 | 128 | — | — | SBL498 | — | — | — |
| KS75 | 8 | 1 | — | SBL634 | — | — | — |
| KS91 | 256 | — | — | SBL635 | — | — | — |
| KS109 | 16 | — | — | SBL648 | 8 | 8 | 8 |
| | | | | SBL666 | 2 | 2 | 2 |
| | | | | SBL668 | 8 | 8 | 8 |
| | | | | SBL680 | — | — | — |
| | | | | SBL691 | — | — | — |
| | | | | SBL692 | — | — | — |
| | | | | SBL698 | 2 | 4 | 2 |
| | | | | SBL705 | — | — | — |

TABLE 1-continued

| Haemagglutination by pyelonephritic and faecal strains of *E. coli*[a] | | | | | | | |
|---|---|---|---|---|---|---|---|
| Pyelone- | Species of erythrocytes | | | | Species of erythrocytes | | |
| phritic strain | hu-man[b] | guinea pig | bo-vine | Faecal strain | hu-man | guinea pig | bo-vine |
| | | | | H10407 | 2 | — | 2 |

[a]Freshly isolated bacteria grown on CFA-agar for 16 h.
[b]Erythrocytes from one individual with blood group A (Rh−)
[c]Haemagglutination titre in the presence or absence of D-mannose (40 mM)

REFERENCES

1. Jones, G. W. (1977) in Microbial Interactions (Reisaig, K. L. ed.), Receptors and Recognition. Series B, Volume 3, pp. 139–176, Chapman and Hall, London.
2. Fowler, J. E. & Stamey, T. (1977). J.Urol. 1, 472–476.
3. Källenius, G. & Winberg, J. (1978). Lancet. ii, 540–543.
4. Källenius, G. & Möllby, R. (1979). FEMS Microbiol. Lett. 5, 295–299.
5. Svenson, S. B. and A. A. Lindberg (1979) J. Immunol. Meth. 25, 323.
6. Zopf, D. et al (1978) Immunol.Meth.enzymol. L, part C, 163171 (Two papers)
7. Lemieux et al (1975) JACS 97:14, 4076.
8. Lönngren, J. et al (1976) Arch.Biochem. Biophys. 175, 661.
9. Svenson, S. B. and A.A. Lindberg (1978) J. Immunol. 120, 1750.
10. Gray, G. R. (1978). In Meth.enzymol. L, part C, 155.
11. Svenson S. B. and K Larsen (1977), J.Immunol.Meth. 17, 249.
12. J. K. N. Jonen and W. W. Reid, J.Chem.Soc. (1955) 1890.
13. D. M. Marcus, N. Naiki and S. K. Kundu. Proc.Nat. Acad.Sci. USA 73 (1976) 3263-3267.
14. Cox, D. D., Metzner, E. K., Reist, E. J. A new synthesis of 4—O—α—D—galactopyranosyl—D—galactopyranose. Carbohydrate Research 62, 245-252 (1978).
15. Shah, R., Bahl, O. Reaction of tetraacetyl α—D—hexopyranoside bromides with sodium nitrophenoxide in DNF. Formation of p-nitrophenyl hexopyranosides ... Carbohydrate Research 74, 105–116 (1979).
16. Cox, D. D., Metzner, K., Reist, E. J. The synthesis of methyl 4—O—(4—O—α—D—galactopyranosyl—β—D—galactopyranosyl)—β—glycopyranoside: The methyl β-glycoside of the trisaccharide related to Fabry's disease. Carbohydrate Research 63, 139–147 (1978).
17. Koenigs, W., Knorr, E. Berichte 34, 957(1901).
18. McBroom, C. R., Samanen, C. H., Goldstein, I. J. In: Methods in Enzymology, Vol. 28B, ed. V. Ginsburg, p. 212. Adademic Press, New York (1972).

We claim:

1. A method for inhibiting the adhesion of uropathogenic bacteria to cells which involves the step of exposing the bacteria to an active principle which is an oligosaccharide compound comprising, in terminal position, a structural element consisting essentially of $$\alpha-D-Gal-(1-4)-D-Gal \quad (I).$$

which structural element is recognized by the uropathogenic bacterial receptor system, wherein the oligosaccharide compound consists essentially of α—D—Gal—(1-4)—D—Gal—(S)$_n$—T$_m$  (III), wherein T is —L—MMB, wherein (S)$_n$ represents one or more additional saccharide moieties, L represents a linking arm covalently attached to the adjacent saccharide moiety, and MMB represents a nontoxic and noninterfering macromolecular carrier covalently attached to said linking arm and selected from the group consisting of proteins, polypeptides, polysaccharides, aliphatic hydrocarbons, and natural and synthetic polymers, or wherein T is —1—OR, wherein R is a nontoxic and noninterfering organic residue, wherein n is zero or an integer, and wherein m is also zero or an integer.

2. Method of claim 1, characterized in that the linking arm between the structural element and the macromolecular carrier is comprised in a structure which consists of:

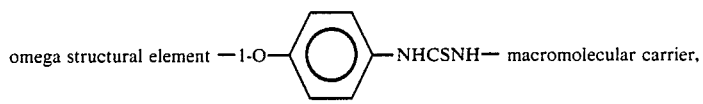

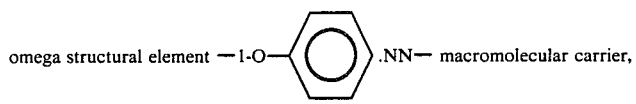

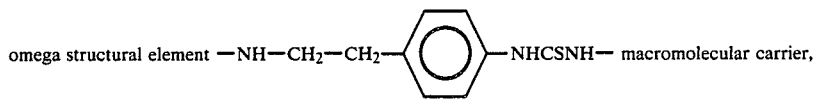

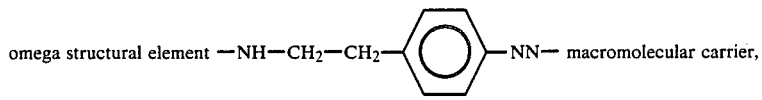

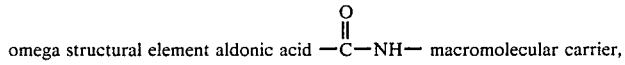

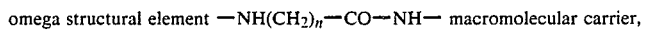

wherein n can vary between 1 and 20, said structural element being bonded to the linking arm by a terminal reducing sugar residue which, in the case of the aldonic acid —CO— group, is in its aldonic acid form.

3. A method for inhibiting the adhesion of uropathogenic bacteria to cells which involves the step of exposing the bacteria to an active principle which is an oligosaccharide compound comprising, in terminal position, a structural element consisting essentially of α—D—Galp—(1-4)—α or β—D—Galp  (Ia), which structural element is recognized by the uropathogenic bacterial receptor system, wherein the oligosaccharide compound consists essentially of α—D—Galp—(1-4)—α or β—D—Galp—(S)$_n$—T$_m$  (IV), wherein T is —L—MMB, wherein (S)$_n$ represents one or more additional saccharide moieties, L represents a linking arm covalently attached to the adjacent saccharide moiety, and MMB represents a nontoxic and noninterfering macromolecular carrier covalently attached to said linking arm and selected from the group consisting of proteins, polypeptides, polysaccharides, aliphatic hydrocarbons, and natural and synthetic polymers, or wherein T is —1—OR, wherein R is a nontoxic and noninterfering lower-aliphatic, nitrophenyl, or ceramide moiety, attached in either alpha or beta configuration, wherein n is zero or an integer, and wherein m is also zero or an integer.

4. A method of claim 3, wherein R is methyl.

5. A method of claim 3, wherein (S)$_n$ is selected from one or more of alpha and beta D-glucose, alpha and beta D glucitol, alpha and beta D-glucopyranosyl, alpha and beta 2-acetamido-2-deoxy-glucopyranosyl, and alpha and beta D-galactopyranosyl, and a further alpha and beta D-glucose moiety.

6. A method of claim 5, wherein R is methyl.

7. Method of claim 3, wherein the said structural element has the formula:

α—D—Galp—(1-4)—β—D—Galp.

8. Method of claim 3, wherein said structural element has the formula:

α—D—Galp—(1-4)—α—D—Galp.

9. Method of claim 3, wherein said structural element plus (S)$_n$—T has the formula:

α—D—Galp—(1-4)—α or
β—D—Galp—1—O—R, wherin R is a nontoxic and noninterfering organic residue which is attached in either alpha or beta configuration.

10. Method of claim 3, wherein said structural element plus (S)$_n$ has the formula:

α—D—Galp—(1-4)—β—D—Galp—(1-4)—D—Glc.

11. Method of claim 3, wherein said structural element plus $(S)_n$ has the formula:

α—D—Galp—(1-4)—β—D—Galp—(1-4)—β—D—Glc.

12. Method of claim 3, wherein said structural element plus $(S)_n$ has the formula:

α—D—Galp—(1-4)—β—D—Galp—(1-4)—α—D—Glc.

13. Method of claim 3, wherein said structural element plus $(S)_n$—T has the formula:

α—D—Galp—(1-4)—β—D—Galp—(1-4)—α or β—D—Glcp—1—O—R.

14. Method of claim 3, wherein said structural element plus $(S)_n$ has the formula:

α—D—Galp—(1-4)—β—D—Galp—(1-4)—D—Glucitol.

15. Method of claim 3, wherein said structural element plus $(S)_n$—T has the formula:

α—D—Galp—(1-4)—β—D—Galp—(1-4)—αD—Glcp—1—O—Me.

or

α—D—Galp—(1-4)—β—D—Galp—(1-4)—β—D—Glcp—1—O—Me.

16. Method of claim 3, wherein said structural element plus $(S)_n$ has the formula:

α—D—Galp—(1-4)—β—D—Galp—(1-4)—β—D—GlcNAcp—(1-3)—β—D—Galp—(1-4)—D—Glc.

17. Method of claim 3, wherein the structural element plus $(S)_n$—T has the formula:

α—D—Galp—(1-4)—β—D—Galp—(1-4)—β—D—Glcp—1—O—Ceramide.

18. Method of claim 3, wherein the structural element plus $(S)_n$—T has the formula:

α—D—Galp—(1-4)—β—D—Galp—(1-4)—β—D—GlcNAcp—(1-3)—β—D—Galp—(1-4)—β—D—Glcp—1—O—Ceramide.

19. Method of claim 3, wherein the structural element plus $(S)_n$—T has the formula:

α—D—Galp—(1-4)—β—D—Galp—1—O—Ceramide.

* * * * *

UNITED STATES PATENT AND TRADEMARK OFFICE
CERTIFICATE OF CORRECTION

PATENT NO. : 4,762,824  Page 1 of 2

DATED : August 9, 1988

INVENTOR(S) : Gunilla P. Källenius, Karl A. Lundblad, Nils R. Möllby, Stefan B. Svensson, Jan Winberg It is certified that error appears in the above-identified patent and that said Letters Patent is hereby corrected as shown below:

Col. 1, line 19; "urophathogenic" should read -- uropathogenic --

Col. 1, line 45; after "recognized" insert a comma -- , --
Col. 1, line 51; delete "which is"
Col. 1, line 52; after "character," insert -- which is --
Col. 1, line 60; "to" should read -- of --
Col. 1, line 61; "function in of cells" should read -- function of cells in --

Col. 1, line 62; after "bacteria" insert -- which are known to be responsible for --
Col. 2, lines 3-6; after "bacteria" insert a period -- . -- and delete the rest of the paragraph (starting with "and" through "adhere.")
Col. 2, line 8; after "strains" and before the period "." insert the following: -- and their recognition of the structural element of the present invention in preference to their recognition of cells to which said bacteria might otherwise adhere --
Col. 2, line 15; "(Jones et al.," should read -- (Jonen et al., --

Col. 2, line 27; "B]" should read -- β] --
Col. 2, line 31; "effect" should read -- affect --
Col. 2, line 63; "--βD--" should read -- --β--D-- --
Col. 4, line 59; "--Cer" should read -- --Cer. --
Col. 5, line 33; "Umea," should read -- Umeå, --
Col. 8, line 64; "conjunction" should read -- conjugation --
Col. 9, line 53; "as" (second occurrence) should read -- or --
Col. 12, line 1; after "erythrocytes" insert a comma -- , --
Col. 12, lines 26 & 27; "hydridoma" should read -- hybridoma --
Col. 14, line 10; "(Rh-)" should read -- (Rh+) --
Col. 14, line 50; after "--β--" (second occurrence) insert -- D-- --
Col. 14, line 57; "Adademic" should read -- Academic --

UNITED STATES PATENT AND TRADEMARK OFFICE
CERTIFICATE OF CORRECTION

PATENT NO. : 4,762,824

DATED : August 9, 1988

INVENTOR(S) : Gunilla P. Källenius, Karl A. Lundblad, Nils R. Möllby, Stefan B. Svensson, Jan Winberg It is certified that error appears in the above-identified patent and that said Letters Patent is hereby corrected as shown below:

Col. 15, approximately line 29 (second formula structure); ".NN—" should read —  —NN—  —

Col. 15, approximately line 43 (fifth formula structure); after "carrier," insert — or —

Col. 17, line 31; "—αD—" should read —  —α—D—  —

Signed and Sealed this

Fourteenth Day of March, 1989

*Attest:*

DONALD J. QUIGG

*Attesting Officer*  *Commissioner of Patents and Trademarks*